(12) United States Patent
Reinhardt et al.

(10) Patent No.: US 6,381,783 B2
(45) Date of Patent: May 7, 2002

(54) HEAD CLAMP

(75) Inventors: Hans F. Reinhardt, Basel (CH); Manfred Fischer; Markus Nesper, both of Tuttlingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/797,194

(22) Filed: Mar. 1, 2001

Related U.S. Application Data

(63) Continuation of application No. PCT/EP99/05922, filed on Aug. 12, 1999.

(30) Foreign Application Priority Data

Sep. 9, 1998 (DE) .......................................... 198 41 250

(51) Int. Cl.⁷ ................................................ A61G 13/12
(52) U.S. Cl. ...................... 5/622; 5/637; 5/640; 5/643
(58) Field of Search ............................. 5/622, 637, 640, 5/643; 602/32, 33, 35, 36, 37

(56) References Cited

U.S. PATENT DOCUMENTS

| | | | |
|---|---|---|---|
| 2,966,383 A | 12/1960 | Boetcker et al. | |
| 3,099,441 A | * 7/1963 | Ries | 5/637 |
| 3,835,861 A | * 9/1974 | Kees, Jr. et al. | 5/637 |
| 4,108,426 A | 8/1978 | Lindstroem et al. | |
| 4,169,478 A | * 10/1979 | Hickman | 5/637 |
| 5,269,034 A | * 12/1993 | Day et al. | 5/622 |
| 5,318,509 A | 6/1994 | Aagbodoe | |
| 5,560,728 A | * 10/1996 | McFadden | 5/637 |
| 6,179,846 B1 | * 1/2001 | McFadden | 602/36 |

FOREIGN PATENT DOCUMENTS

| | | |
|---|---|---|
| DE | 91 07 609 | 9/1991 |
| DE | 43 42 971 | 3/1995 |
| EP | 0 522 242 | 11/1995 |
| GB | 2 305 364 | 4/1997 |

* cited by examiner

Primary Examiner—Michael F. Trettel
(74) Attorney, Agent, or Firm—Barry R. Lipsitz

(57) ABSTRACT

The invention relates to a head clamping device (1) comprising a frame composed of two elements (2,3) exhibiting each first ends (7) flexibly connected to each other and second ends (5) with spikes (13,19) for fixing the head. The aim of the invention is to increase the mechanical stability of such a device. For that purpose, the frame elements (2,3) are mounted in such a way that they can rotate relatively to each other around a common rotation axis (4).

25 Claims, 3 Drawing Sheets

HEAD CLAMP

This application is a continuation of international application number PCT/EP99/05922 filed on Aug. 12, 1999.

The invention concerns a head clamp for positioning a head, with a frame formed from two frame elements, which respectively have first ends which are movably joined together and second ends which carry pins for fixing the head in position.

In the case of the already known head clamps of the type initially described, the head is clamped between the two frame elements, i.e., by a linear movement of the two frame elements relative to one another. For the purpose of positioning the head, it is first brought between the two frame elements and the two frame elements are then moved axially towards one another by means of a side arm of each of the frame elements. The frame elements are locked relative to one another for the purpose of initial fixing in position. The head is finally clamped by means of a fine adjustment of the pins in which the latter are moved yet further on to the head.

The disadvantages of these head clamps are to be seen primarily in the large amount of mechanical play of the frame elements relative to one another; the longer the side arms that are in contact with one another, the greater is this play. Moreover, the adjustment and retightening of the pins by screwing is demanding and awkward. Also disadvantageous is the increased risk of breakage with increased loading, particularly through the attachment of additional appliances. These head clamps are also unsuitable for additional neuroradiological examinations, since they substantially restrict the beam path.

Accordingly, the object of the present invention is to develop a head clamp of the generic type in such a way that a greater mechanical stability is achieved.

This object is achieved, in the case of a head clamp of the type initially described, according to the invention in that the frame elements are pivoted relative to one another about a common axis of rotation.

For the purpose of clamping the head, the two frame elements are swivelled relative to one another, about a common axis of rotation. This enables the frame elements to be dimensioned as small as possible since, unlike those of head clamps which are adjustable in the axial direction, the side arms of the frame elements do not have to be made longer in order to permit opening of the head clamp. Due to the relative swivelling of the frame elements, a maximum opening angle can consequently be set with a very small structural size. This facilitates the handling and the application of the head clamp. In addition, the weight of the head clamp is drastically reduced, since the frame elements can be made substantially smaller and shorter. Due to a smaller structural form of the head clamp achieved thus, its mechanical stability is increased substantially in comparison with those already known in the art.

According to a preferred embodiment of the present invention, provision can be made such that the frame comprises a swivel position fixing device with at least one fixing component, on one of the two frame elements, which has at least one projection, and with corresponding recesses, disposed on the other frame element, in which the projection engages in a fixing position and fixes the frame elements in their position relative to one another, and that the fixing component can be brought relative to the recesses from the fixing position into a release position in which the frame elements can be swivelled relative to one another.

This design of the head clamp enables the frame elements to be fixed in a defined position relative to one another. It is thus possible to define the relative swivelling of the frame elements solely through the interaction of the fixing component with the recesses, for example, solely through the movement of the projection of the fixing component into the recess. As soon as the fixing component is withdrawn from the recesses, the frame elements can be swivelled again as required.

It is then advantageous if the recesses are connected non-rotatably to the other frame element. The non-rotatable connection has the advantage, firstly, of making the position fixing as free of play as possible, since a relative degree of freedom for a movement between the recesses and the frame element of the head clamp is thus eliminated. In addition, there is no need for a further, complicated, locking mechanism since the projections of the fixing components of the one frame element engage directly in the recesses and, in this way, are joined directly to the other frame element.

It is particularly advantageous if the fixing component is movable relative to both frame elements. The fixing component that is movably joined to the one frame element can thus engage in the recesses of the other frame element and remain invariably joined to the one frame element.

According to an advantageous embodiment, there can be provision such that the fixing component can be moved by means of an actuating component joined to it with a positive fit. The advantage lies in the fact that the fixing component can be concealed. Only the actuating component need be accessible to a person operating the head clamp. In addition, to facilitate actuation of the fixing component, an appropriate lever is provided on the actuating component. Furthermore, it is conceivable that one or more fixing components can be moved by a single actuating component. A quick-action mechanism is thus achieved for the head clamp.

In the case of another preferred embodiment of the invention, provision can be made such that the fixing component is mounted on a frame element in such a way that it can be moved towards the recesses. The swivelled head clamp can thus be fixed in its position solely by the fixing component being pushed into the recess. This renders possible particularly fast and easy handling of the head clamp.

In the case of another embodiment of the invention, provision can be made such that the fixing component is mounted on the one frame part in such a way that it can be swivelled towards the recesses. A pivoted mounting of the fixing component allows levers, resulting from this type of mounting, to be used on the fixing component, rendering possible a particularly force-efficient locking or release by means of the fixing component.

It is particularly advantageous if the recesses are formed by the teeth of a toothed wheel whose circumference extends maximally over an angular range of 360°. Toothed wheels can be produced very simply and cost-effectively by machine. In addition, it can be sufficient to provide only a limited angular range of the toothed wheel with teeth for which fixing of the head clamp in its position is required. This also reduces the production expenditure.

It is then advantageous if the teeth are undercut on at least one side. This has the advantage that when the fixing component is engaged between the teeth of the toothed wheel, inadvertent removal of the fixing component from the recess becomes impossible if the head clamp is pretensioned. An additional safeguard is thus provided against unintentional release of the fixing position.

According to a preferred embodiment of the invention, provision can be made such that only one of the fixing components can be brought into the fixing position in each case. A more precise subdivision for possible swivel positions of the head clamp can thus be predefined with appropriate arrangement of the fixing components relative to the recesses. This means, firstly, that the number of fixing positions can be increased and, secondly, that the fixing components and the corresponding recesses can be made sufficiently large to permit an optimal transfer of force. In addition, the play of the frame elements in relation to one another is reduced and the mechanical stability of the head clamp is coincidentally increased.

It is advantageous if the projections on the fixing components are in each case offset, according to the number of fixing components by a fraction, which is the reciprocal of this number, of a tooth division of this toothed wheel. The number of teeth of the tooth wheel is thus in effect multiplied by a factor corresponding to the number of fixing components. This means, for example, that in the case of there being 20 teeth on a quarter-circle circumference and there being four fixing components, a possible number of 80 fixing positions is obtained. Instead of increasing the number of teeth and consequently reducing the size of the recesses, the teeth can be made larger, with the result that the stability of the head clamp is increased and greater forces can be taken up by the swivel position fixing device.

Provision can by made in principle such that the swivel position fixing device has at least one elastic pressure element which holds the fixing component in the fixing position. It is thus ensured that the frame elements stay fixed in position relative to one another. Consequently, it is then only necessary to move the fixing components when the frame elements are to be swivelled relative to one another.

Above all, this offers the safeguard that fixing of the frame elements in position is not forgotten. An operator wishing to swivel the head clamp into any desired position must first release all fixing components, for example by means of the actuating component. Otherwise, the fixing components are held in the recesses by the pressure element.

It is then advantageous if the elastic pressure element is formed by a leaf spring. A leaf spring can be produced cheaply and is simple to mount. In addition, a leaf spring has relatively large bearing faces. Several fixing components can thus also be held simultaneously in the fixing position by one leaf spring.

In the case of a preferred embodiment of the present invention, provision can be made such that all fixing components can be brought simultaneously into their release position by the actuating component. This provides for a rapid adjustment of the swivel position. If the actuating component is not actuated the fixing components lock in the recesses and the head clamp is fixed in a defined swivel position. It is only through actuation of the actuating component that all fixing components are brought simultaneously into their release position. The frame elements of the head clamp can then be swivelled relative to one another.

Provision can be made in principle such that a frame element has a frame part and a support part joined to the latter, that the frame part and the support part can be pivoted about the common axis of rotation and define a swivel angle and that the frame part can be fixed in position relative to the support part for each possible swivel angle. No further fine adjustment on the head clamp is possible by the fixing of a swivel position as described above by means of fixing components and corresponding recesses. Such a fine adjustment becomes possible only through the division of the frame element into the frame part and the support part. By contrast with the swivel position fixing device, each possible swivel angle can be fixed between the frame part and the support part. The pins can thus be brought into each possible position for locating a head.

Provision can then be made such that the frame part can be swivelled and fixed in position in a defined manner relative to the support part by means of a swivel angle adjusting device and that the swivel angle adjusting device can be adjusted by a screwed connection. The additional screwed connection enables the frame part to be both swivelled and fixed in position relative to the support part. The main advantage of this design is that fine adjustment of the head clamp is possible by means of a single screwed connection. Moreover, no further screwed connections are necessary.

It is particularly advantageous if the fixing components are disposed on the support part. The joining of the support part to the frame part enables the frame part to be swivelled relative to the other frame element. This swivel position is fixed by means of the fixing components disposed on the support part and the recesses disposed on the other frame element. The support part is thus fixed in its position relative to the other frame element. On this basis, the frame part can be swivelled and fixed in position relative to the support part by means of the screwed connection. Coarse setting of the head clamp is thus effected by means of a movement of the support part relative to the other frame element, fine adjustment being effected by means of a movement of the support part relative to the frame part joined to it.

Provision can be made in principle such that the frame elements have passage openings for a bearing shaft, defining the axis of rotation, and form a slide bearing with it. The sliding arrangement of the frame elements reduces to a minimum the tilt play transversely relative to the axis of rotation. In addition, the axis of rotation is defined by the axis of symmetry of the bearing shaft.

It is then advantageous if in the region of the bearing shaft the frame elements have slide faces, running transversely relative to the axis of rotation, by means of which they bear on one another. The frame elements can thus be supported on one another in the region of the axis of rotation. The sliding mounting without play on the bearing shaft and the slide faces bearing on one another can also reduce the tilt play.

It is particularly advantageous if a frame element is rigidly joined to the bearing shaft. An additional play between this frame element and the bearing shaft is thus rendered impossible at the outset, increasing the mechanical stability of the head clamp.

Provision can be made in principle such that the frame elements are fixed in position relative to one another in the direction of the axis of rotation. Thus, the frame elements cannot be separated from one another in the direction of the axis of rotation. This fixing can be used to set a required, if small, play between the frame elements and the bearing shaft, but only to the extent that there can be no tilting of the frame elements relative to one another.

According to a preferred embodiment of the invention, provision can be made in principle such that the frame elements are essentially L-shaped. This shape of the frame elements is particularly advantageous for optimally surrounding a head. In addition, the L-shape offers essentially two straight side sections to which further ancillary instruments can be attached.

It is advantageous if at the free end the one frame element has a pin whose longitudinal axis points essentially towards the free end of the other frame element. This alignment of the pin axis affords an optimal transfer of force from the frame element to the head via the pin.

It is advantageous if in that at its free end the other frame element has a rocker mounting whose longitudinal axis points essentially towards the free end of the other frame element, if the rocker mounting has an essentially C-shaped bow which is pivoted, transversely relative to its longitudinal axis, in its central region and if at each of its free ends the bow has a pin which points essentially towards the free end of the other frame element. Due to the shifting of the rough adjustment and fine adjustment to a base of the head clamp, it is no longer necessary to make the pins separately adjustable. Any required swivel angle between the frame elements can be compensated by means of the rocker mounting in such a way that the pin on the other frame element points exactly in each case towards the pivoted central region of the bow. It would also be conceivable for the rocker mounting to be mounted on the frame element so that it is rotatable about its longitudinal axis and can be fixed in any possible rotation position by means of a locking device. It is also possible to interchange the single pin with the rocker mounting, depending on the amount of space required for additional instruments having to be attached to the head clamp.

According to a preferred embodiment of the invention, provision can be made such that in cross section the frame elements have a profile which is shaped to complement the profile of a corresponding receiver of a standard mounting for further instruments. The head clamp thus becomes universally applicable for already existing mountings for positioning further instruments.

It is also advantageous if in the region of the axis of rotation the frame elements have on their respective exteriors a profile which is shaped to complement the profile of a receiver of a standardized head clamp holding device. Due to this special profiling, the head clamp can also be clamped into the head clamp holding devices already used for conventional head clamps. This enables the head clamps of the type initially described to be replaced by the newly proposed head clamps, using the existing head clamp holding devices.

The invention is described more fully with reference to the following description of a preferred embodiment in combination with the drawing, wherein.

Figure 1:
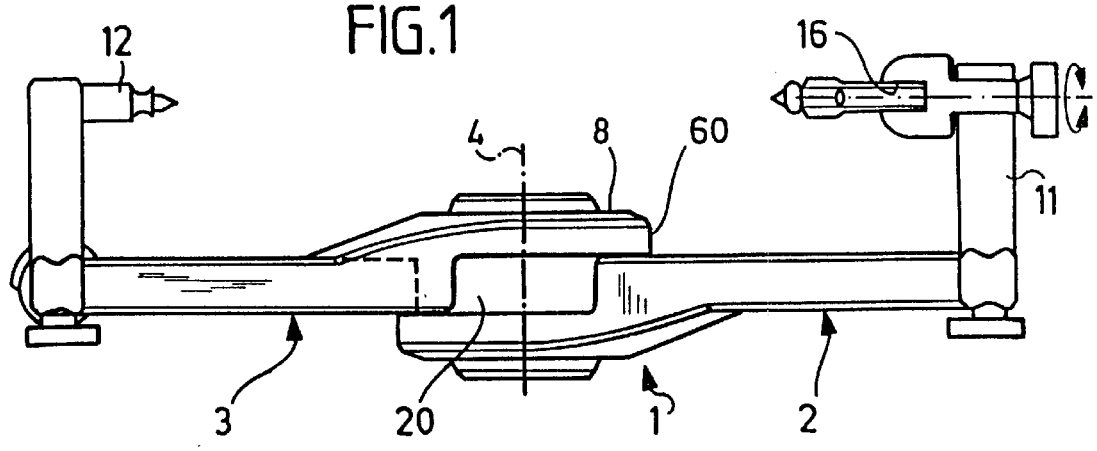
FIG. 1 shows a side view of a head clamp in a direction perpendicular to the axis of rotation.
Figure 2:
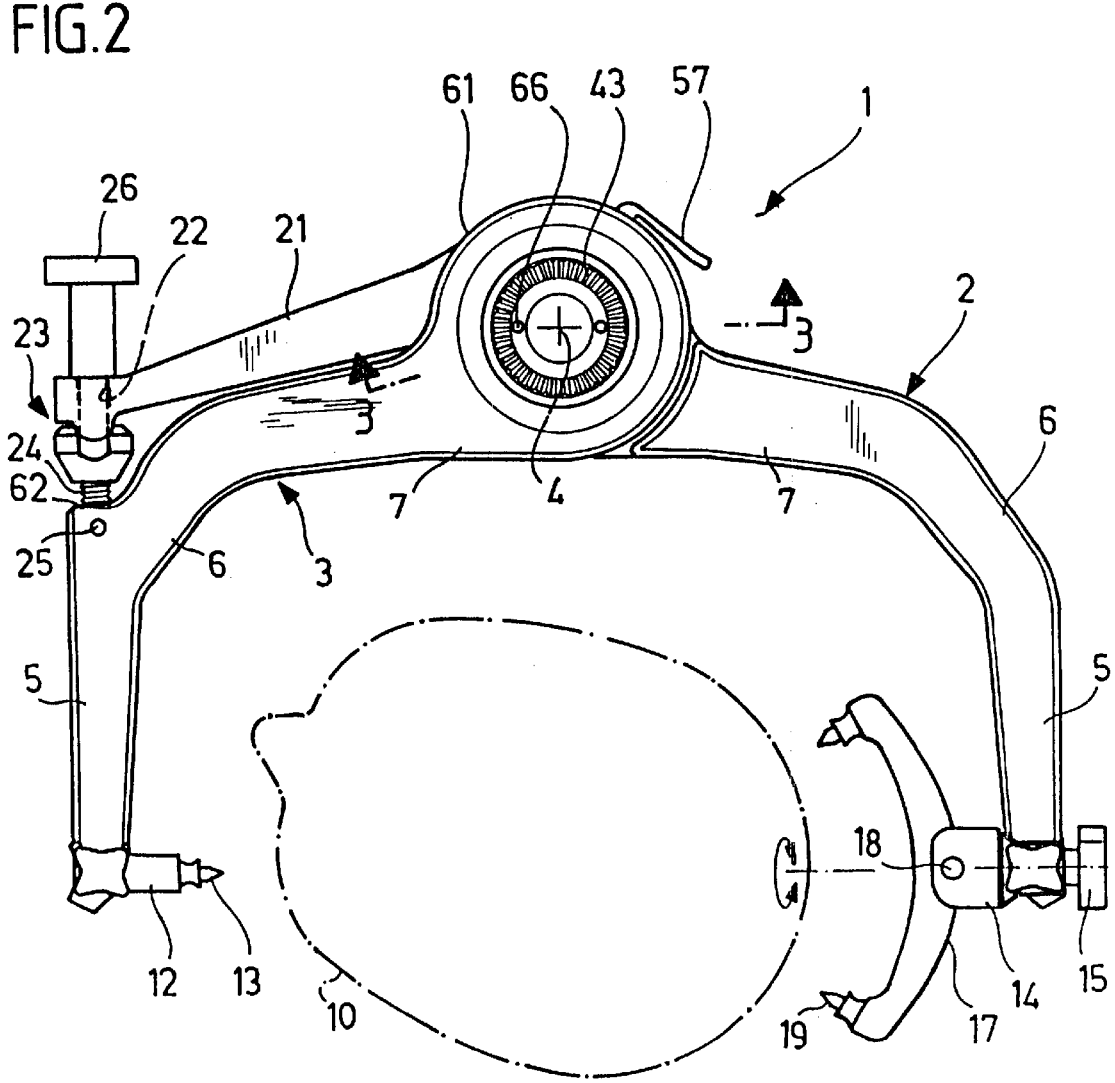
FIG. 2 shows a side view of a head clamp in the direction of the axis of rotation.

FIGS. 1 and 2 depict a head clamp, denoted in general by the reference 1, which is formed essentially by two virtually identical L-shaped clamping bows 2 and 3. The two clamping bows 2 and 3 can be swivelled relative to one another about an axis of rotation 4. The clamping bows 2 and 3 formed by three rectilinear bow sections have an essentially rectangular cross section. Proceeding from an end section 5, there is a middle section 6 which is bent at about 45° and which, after a further rounded bend of 45°, merges into a base section 7. This results in an essentially L-shaped clamping bow 2 or 3. The sections 5 to 7 are essentially identical in length.

Joined to the free end of the base section 7 and laterally offset in relation to it is a bearing receiver 8 which has a bearing bore 9, rotatably symmetrical in relation to the axis of rotation 4, its diameter corresponding approximately to half the diameter of the bearing receiver 8. The thickness of the bearing receiver 8 in the direction of the axis of rotation 4 corresponds approximately to the thickness of the base section 7 in the direction of the axis of rotation 4. In addition, the side of the base section 7 of the clamping bow 2 or 3 forming the 90° angle with the end section 5 merges tangentially into the outer circumferential wall 60 of the bearing receiver 8.

The two clamping bows 2 and 3 thus form an essentially C-shaped head clamp 1 which, for the purpose of positioning a head 10, surrounds it in the form of a half ring. The non-symmetrical arrangement of the bearing receivers 8 on the base sections 7 results in a semicircular projection 61 of the bearing receivers 8 on the side of the head clamp 1 that faces away from the head 10.

Disposed at the free ends of the end sections 5 are bearing posts 11 which extend outwardly on one side in parallel to the axis of rotation 4. In addition, at the end of a pin mounting 12 which extends perpendicularly outwards from the bearing post 11 and the end section 5, the bearing post 11 joined to the clamping bow 3 carries a single pin 13 which forms the extension of the rotatably symmetrical pin mounting 12 and points towards the opposing bearing post 11 disposed on the clamping bow 2.

Disposed at the end of the bearing post 11 of the clamping bow 2 is rocker mounting 14 which, in a manner similar to the pin mounting 12, extends outwards from the bearing post 11 on one side and points towards the pin mounting 12. The rocker mounting 14 is mounted on the end section 5 of the clamping bow 2 so as to be rotatable about its longitudinal axis and can be fixed in position with a locking screw 15 disposed on the side of the head clamp 1 that faces away from the head 10. On its side which faces towards the head 10 the rocker mounting 14 has a receiving groove 16 in which a C-shaped rocker bow 17 is pivoted in a plane which runs parallel to the plane enclosed by the clamping bows 2 and 3. The fact that the rocker mounting 14 is mounted so that it is rotatable about its longitudinal axis and can be fixed in position also enables the rocker bow 17 to be swivelled in a plane which does not run parallel to the plane enclosed by the clamping bows 2 and 3. The swivelling axis of the rocker bow 17, which is curved away from the rocker mounting 14, is formed by the axis of symmetry of a bearing pin 18, the axis of symmetry of the bearing pin 18 running parallel to a longitudinal axis of the bearing post 11. The rocker bow 17, which is mounted at its central region, has at each of its free ends a clamping pi n 19 which extends outwards from the rocker bow 17, transversely relative to the curvature of the latter, and points approximately towards the centre of the head 10.

Due to the lateral offset of the bearing receivers 8 relative to the base sections 7, an essentially cylindrical free region is formed. Projecting into the latter and joining the bearing receivers 8 with a positive fit is a bearing receiving part 20, of cylindrical outer contour, which tangentially joins the end of a support carrier 21, in a manner similar to the bearing receiver 8. The bearing receiving part 20 and the support carrier 21 run in the same plane as the three sections 5, 6 and 7. The support carrier 21 extends essentially in parallel to the base section 7 of the clamping bow 3, but is of such a length that it projects somewhat over the imagined extension of the end section 5.

This free end of the support carrier 21 has a bore 22, the axis of symmetry of which points towards the longitudinal axis of the end section 5. Disposed in this bore 22 is a spindle drive 23, not depicted in greater detail, which is joined to the clamping bow 3 through a joining component 24. The joining component 24 engages in the frame element 3 at a shoulder 62 of the end section 5, in the transitional region between the middle section 6 and the end section 5, and it is also pivoted, in the plane enclosed by clamping bows 2 and 3, about a further bearing pin 25. The clamping bow 3 can be swivelled about the axis of rotation 4, relative to the support carrier 21, by rotation of an adjusting screw 26.

Figure 3:
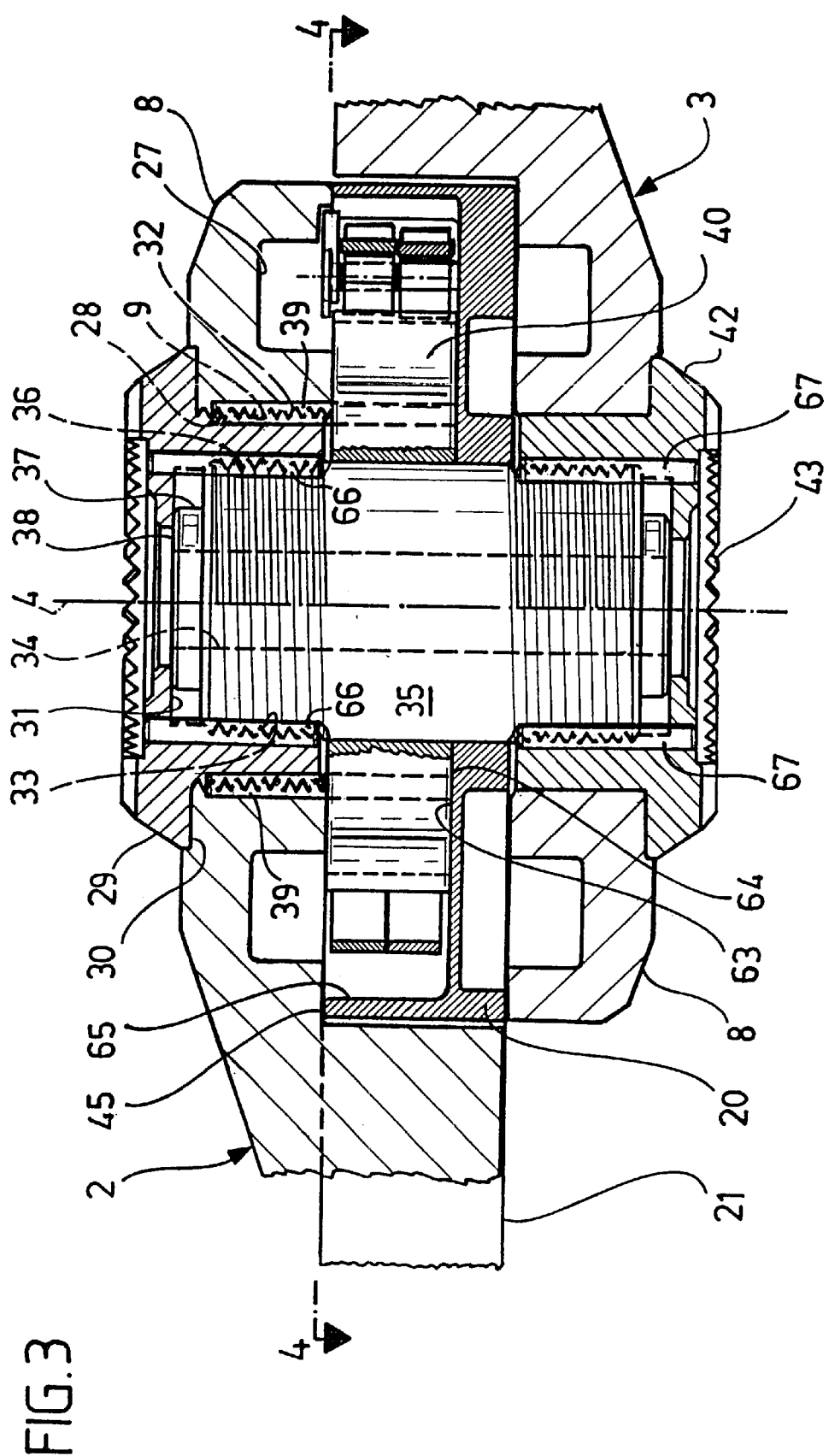
FIG. 3 shows a side view through a head clamp, along the line 3—3 from FIG. 2.
Figure 4:
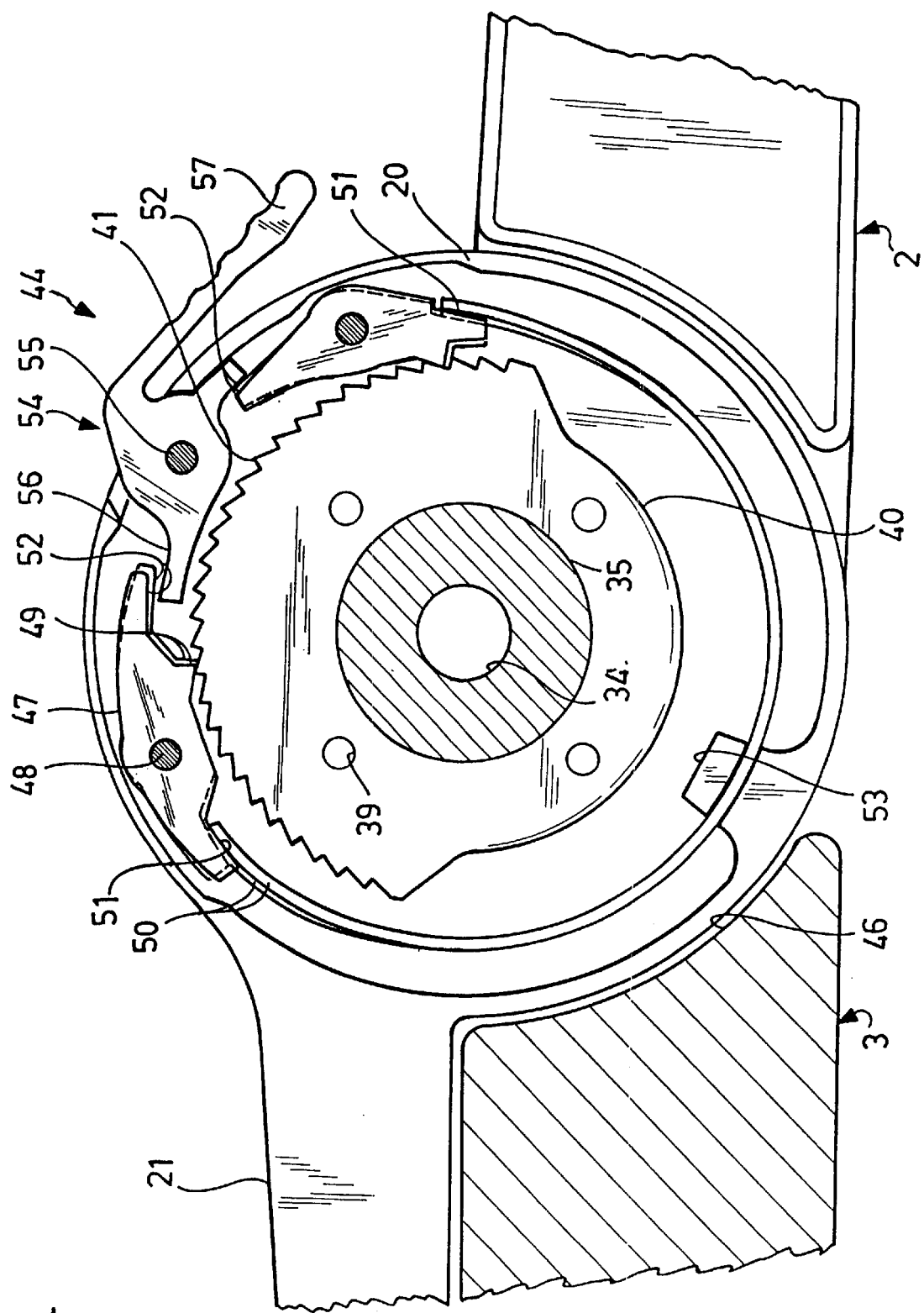
FIG. 4 shows a cross sectional view along the line 4—4 from FIG. 3.

Only the geometry of the head clamp 1 has been described in detail thus far. The following describes how the clamping bows 2 and 3 can be swivelled relative to one another. For this purpose, FIGS. 3 and 4 depict in detail the joining of the clamping bows 2 and 3 in the region of the axis of rotation 4.

Both bearing receivers 8 of the clamping bows 2 or 3 have an annular groove 27, each of which is open towards the bearing receiving part 20. The bearing receiver 8 of the clamping bow 2 is provided with an internal screw thread 28. Screwed into the bearing bore 9 of the clamping bow 2 which is provided with the internal screw thread 28 is a bearing sleeve 29 from which, on the side facing away from the bearing receiving part 20, there extends radially, away from the axis of rotation 4 and beyond the diameter of the sleeve, a projection 30 which serves as a stop of the bearing sleeve 29 on the bearing receiver 8. Extending towards the axis of rotation 4 in the extension of the projection 30 is a shaft stop 31. In addition, the bearing sleeve 29 has an external screw thread 32 corresponding to the internal screw thread 28. The bearing sleeve 29 is additionally provided with an internal screw thread 33.

A cylindrical bearing shaft 35, provided with a central shaft bore 34, is provided at both ends with an external screw thread 36 which in each case extends over approximately one third of the length of the bearing shaft 35. Beyond the region of the external screw thread 36 the diameter of the bearing shaft 35 decreases in a single stage. This shaft section 37 has no thread. One end of the bearing shaft 35 is screwed into the internal screw thread 33 of the bearing sleeve 29, contacting the shaft stop 31 with an end edge 38 of the shaft section 37.

The screwed joint between the bearing receiver 8 and the bearing shaft 35 is additionally secured against unintentional twisting by means of two locking pins 66. The locking pins 66 are inserted from the outside, in parallel to the axis of rotation 4, through bores which are diametrically opposite one another relative to the axis of rotation 4. The bores for the locking pins 66 are disposed so that they act on both the internal screw thread 33 of the bearing sleeve 29 and the external screw thread 36 of the bearing shaft 35. The bearing shaft 35 is thus non-rotatably connected to the bearing sleeve 29.

Between its two ends provided with the external screw thread 36 the bearing shaft 35 is smooth. Proceeding from the described screwed connection with the bearing sleeve 29, the smooth section of the bearing shaft 35 is surrounded, on approximately two thirds of its extent in the axial direction, by a toothed wheel 40 which is provided with teeth 41, undercut on one side, on approximately half of its circumference. The toothed wheel 40 is non-rotatably connected to the bearing sleeve 29 and the bearing receiver 8 by means of four locking pins 39. The locking pins 39 are inserted in bores which are disposed, in pairs which are each diametrically opposite in relation to the axis of rotation 4, in the region of the external screw thread 32 of the bearing sleeve 29 and of the internal screw thread 28 of the bearing receiver 8. In assembly, the bearing sleeve 29 is first screwed into the bearing receiver 8 and the toothed wheel 40 is then positioned. The three parts are then provided with four bores, as described. The toothed wheel 40 is thus non-rotatably connected to the bearing sleeve 29 and the bearing receiver 8 is non-rotatably conencted, by means of the locking pins 39 and, additionally, by means of the locking pins 66, to the bearing shaft 35.

On the remaining third of the threadless section of the bearing shaft 35, the latter is surrounded by the bearing receiving part 20 which has an inner diameter which corresponds to the outer diameter of the bearing shaft 35. The bearing receiving part 20 can thus be twisted, essentially free from play, in relation to the bearing shaft 35.

On the other side, the bearing shaft 35 is screwed to a sliding-bearing sleeve 42, in a manner similar to that described above for the bearing sleeve 29. The screwed connection is similarly secured by means of locking pins 67. Unlike the bearing sleeve 29, however, the sliding-bearing sleeve 42 does not have an external screw thread. Rather, its outer diameter corresponds to the inner diameter of the threadless bearing receiver 8 of the clamping bow 3 in which the sliding-bearing sleeve 42 engages. The clamping bow 3 is thus pivotally mounted relative to the sliding-bearing sleeve 42. The sliding-bearing sleeve 42 is screwed into the bearing receiver 8 just to the extent that there is no remaining play in the axial direction between the projection 30, the bearing receiver 8 and the bearing receiving part 20, but that mutual swivelling of the two clamping bows 2 and 3 and support carrier 21 is still possible. The bores for the locking pins 67 are drilled out only when the sliding-bearing sleeve 42 has been screwed on to the bearing shaft 35 and the swivelling of the two clamping bows 2 and 3 support carrier 21 has been set without play.

The outer end faces of the bearing sleeve 29 and sliding-bearing sleeve 42 are provided with toothed profile inserts 43, in the form of circular discs, whose teeth point outwards in the direction of the axis of rotation 4. They serve as a standardized receiving element for fastening the head clamp 1 to a basic unit, not depicted, for example a mounting on an operating table.

The above describes only how the support carrier 21 can be adjusted relative to the clamping bow 3 by means of the spindle drive 23. Relative to these two parts, the clamping bow 2 can be swivelled quite freely. For the purpose of fixing its position relative to the support carrier 21 and the clamping bow 3, a locking device is provided which is denoted in general by the reference 44 and depicted in detail in FIG. 4.

This locking device 44 acts directly between the bearing receiving part 20 and the toothed wheel 40. In the region of the bearing shaft 35, the toothed wheel 40 and the bearing receiving part 20 slide against one another by means of radial faces 63 and 64. In the outer region of the bearing receiving part 20, the latter extends as a limiting sleeve 65 over the entire region extending axially between the two bearing receivers 8, the bearing receivers 8 being supported on the end faces 45 of the bearing receiving part 20. These end faces 45 act simultaneously as sliding faces. The base sections 7 of the clamping bows 2 and 3 which face towards the bearing receiving part 20 have an outer contour 46 which is matched to the outer diameter of the limiting sleeve 65 of the bearing receiving part 20. In order to permit ease of turning, the outer diameter. of the limiting sleeve 65 of the bearing receiving part 20 is slightly smaller than the inner diameter of the outer contour of the base section 7.

The limiting sleeve 65 of the bearing receiving part 20 thus surrounds the toothed wheel 40 on its entire circumference, but the wall thickness of the limiting sleeve 65 of the bearing receiving part 20 is so small that a distance from the toothed wheel 40 remains which amounts to approximately one quarter of the radius of the toothed wheel 40. Four locking pawls 47 are pivotally mounted in this free region, on the bearing receiving part 20. Provided for each two locking pawls 47 is a common locking pin 48 whose longitudinal axis runs parallel to the axis of rotation 4. The locking pawls 47 have an essentially curved outer contour, facing the inner circumferential wall of the limiting sleeve, which permits swivelling within the free region of the bearing receiving part 20. The locking pins 48 for mounting of the four locking pawls 47 are disposed in the free region of the bearing receiving part 20, each offset by approximately 90° in the circumferential direction of the limiting sleeve 65. Each of the locking pawls 47 has a tooth-type pawl projection 49 facing the toothed wheel 40. These pawl projections 49 are disposed on the locking pawls 47 in such a way that only one pawl projection 49 in each case can engage fully between two teeth 41 of the toothed wheel 40. In the case of the present four locking pawls 47, the pawl projections 49 are each offset by one quarter of the tooth spacing of two teeth 41. The pawl projections 49 of all four locking pawls 47 are pressed simultaneously against the toothed wheel 40 by two leaf springs 50, the leaf spring 50 in each case bearing on a side face of a circumferentially extending pressure projection 51 of the locking pawl 47. The leaf spring 50 itself is located on a spring mounting projection 53 which extends from the circumference of the limiting sleeve 65 of the bearing receiving part 20 towards the axis of rotation 4. This spring mounting projection 53 is disposed approximately diametrically relative to the two locking pins 48 on the opposite side of the bearing shaft 35.

The locking pawl 47 also has a release projection 52 which is disposed on the other side of the locking pin 48 as viewed from the pressure projection 51 and likewise extends in the circumferential direction of the limiting sleeve 65. A common release device 54 is provided for all locking pawls 47. The release device 54 is pivoted about a release pin 55 which is disposed in parallel to the locking pins 48 on the bearing receiving part 20. The release device 54 disposed between the two locking pawls 47 has two unlatching projections 56, extending in the circumferential direction, which bear on the release projections 52 of the locking pawls 47. A release lever 57 joined to the release device 54 projects from the bearing receiving part 20 and extends essentially tangentially from the latter in the circumferential direction of the limiting sleeve 65. The release device 54 can be swivelled about the release pin 54 by a movement of the release lever towards the axis of rotation 4, as a result of which the unlatching projections 56 press against the release projections 52 which, in turn, results in a swivelling of the locking pawls 47. Upon letting go of the release lever 57, the locking pawls 47 are swivelled back into the locating position and the pawl projection 49 again engages between two teeth 41 of the toothed wheel 40.

The locking device 44 thus renders possible a coarse adjustment of the two clamping bows 2 and 3 relative to one another. To apply the head clamp 1, the release lever 57 of the release device 54 is first operated. The two clamping bows 2 and 3 can now be swivelled as required. The head clamp 1, opened thus, is brought to the head 10 and the clamping bows 2 and 3 are swivelled towards one another until the single pin 13 and the clamping pins 19 bear on the head 10. In swivelling to close the head clamp 1 it is not necessary to maintain pressure on the release lever 57. This is because the pawl projections 49 slide on the non-undercut flanks of teeth 41 of the toothed wheel 40 until they slip under the undercut flanks of the then next tooth 41 of the toothed wheel 40. When the clamping bows 2 and 3 can no longer be swivelled further towards one another, the adjusting screw 26 of the spindle drive 23 is turned to swivel the clamping bow 3 relative to the support carrier 21 until the head 10 is clamped immovably between the single pin 13 and the clamping pins 19. Unintentional release of this pretensioned position of the head clamp 1 is impossible since one of the four pawl projections 49 is firmly wedged between two teeth 41, behind the undercut flank of one tooth 41.

By contrast with conventional head clamps, the present embodiment offers the advantage that a large and therefore reliable pressure spring, not depicted, is used for pretensioning the support carrier 21 relative to the clamping bow 3 towards the joining component 24. The fact that the pressure spring which can be regulated by means of the adjusting screw 26 is disposed on a base section 7 of the clamping bow 3 has the additional advantage that the spring element does not interfere with either the cover area of the operation or the beam path for intro-operative X-ray examinations. At worst, the pressure spring can still be retightened from the non-sterile operating area.

The pin mounting 12 and the rocker mounting 14 are freely replaceable and, if necessary, can also be attached to the opposing end section 5.

For intro-operative X-ray diagnostics, including computer tomography, the bearing posts 11 can be mounted and replaced from both sides of the head clamp 1. The neurocranium, i.e., the brain to the base of the skull, can thus be displayed with a large degree of freedom in the anterior, posterior and lateral beam path. The elements which fix the head in position, for example the pin mounting 12, the single pin 13, the rocker bow 17, the rocker mounting 14, the clamping pins 19, etc., are preferably made from X-ray-tolerant titanium.

For the attachment of auxiliary appliances, all laterally accessible parts of the head clamp 1 have an identical receiving profile for gripper elements for attaching mountings for the navigation system, for hand rests, etc. These parts of the head clamp 1 such as, for example, the end section 5, the middle section 6 and the base section 7, are dimensioned accordingly for greater strength.

What is claimed is:

1. Head clamp for positioning a head, with a frame formed from two frame elements, which respectively have first ends which are movably joined together and second ends which carry pins for fixing the head in position, the frame elements being pivoted relative to one another about a common axis of rotation, wherein the frame comprises a swivel position fixing device with at least one fixing component, on one of the two frame elements, which has at least one projection, and with corresponding recesses, disposed on the other frame element, in which the projection engages in a fixing position and fixes the frame elements in their position relative to one another, and the fixing component can be brought relative to the recesses from the fixing position into a release position in which the frame elements can be swivelled relative to one another.

2. Head clamp according to claim 1, wherein the recesses are non-rotatably connected to the other frame element.

3. Head clamp according to claim 1, wherein the fixing component is movable relative to the two frame elements.

4. Head clamp according to claim 3, wherein the fixing component is movable by means of an actuating component joined to it with a positive fit.

5. Head clamp according to claim 1, wherein the fixing component is mounted on the one frame element so that it can be moved towards the recesses.

6. Head clamp according to claim 1, wherein the fixing component (47) is mounted on the one frame element (3) so that it can be swivelled towards the recesses (41).

7. Head clamp according to claim 1, wherein the recesses are formed by the teeth of a toothed wheel whose circumference extends maximally over an angular range of 360°.

8. Head clamp according to claim 7, wherein the teeth are undercut on at least one side.

9. Head clamp according to claim 1, wherein only one of the fixing components can be brought into the fixing position in each case.

10. Head clamp according to claim 7, wherein the projections on the fixing components are in each case offset, according to the number of fixing components by a fraction, which is the reciprocal of this number, of a tooth division of the toothed wheel.

11. Head clamp according to claim 1, wherein the swivel position fixing device has at least one elastic pressure element which holds the fixing component in the fixing position.

12. Head clamp according to claim 11, wherein the elastic pressure element is formed by a leaf spring.

13. Head clamp according to claim 4, wherein all fixing components can be brought simultaneously into their release position by the actuating component.

14. Head clamp according to claim 1, wherein a frame element has a frame part and a support part joined to the latter, the frame part and the support part can be pivoted about the common axis of rotation and define a swivel angle and the frame part can be fixed in position relative to the support part for each possible swivel angle.

15. Head clamp according to claim 14, wherein the frame part can be swivelled and fixed in position in a defined manner relative to the support part by means of a swivel angle adjusting device and the swivel angle adjusting device can be adjusted by a screwed connection.

16. Head clamp according to claim 14, wherein the fixing components are disposed on the support part.

17. Head clamp according to claim 1, wherein the frame elements have passage openings for a bearing shaft, defining the axis of rotation, and form a slide bearing therewith.

18. Head clamp according to claim 17, wherein in the region of the bearing shaft the frame elements have slide faces, running transversely relative to the axis of rotation, by means of which they bear on one another.

19. Head clamp according to claim 17, wherein a frame element is rigidly joined to the bearing shaft.

20. Head clamp according to claim 1, wherein the frame elements are fixed in position relative to one another in the direction of the axis of rotation.

21. Head clamp according to claim 1, wherein the frame elements are essentially L-shaped.

22. Head clamp according claim 1, wherein at the free end the one frame element has a pin whose longitudinal axis points essentially towards the free end of the other frame element.

23. Head clamp according to claim 1, wherein at its free end the other frame element has a rocker mounting whose longitudinal axis points essentially towards the free end of the other frame element, the rocker mounting has an essentially C-shaped bow which is pivoted, transversely relative to its longitudinal axis, in its central region and at each of its free ends the bow has a pin which points essentially towards the free end of the other frame element.

24. Head clamp according to claim 1, wherein in cross section the frame elements have a profile which is shaped to complement the profile of a corresponding receiver of a standard mounting for further instruments.

25. Head clamp according to claim 1, wherein in the region of the axis of rotation the frame elements have on their respective exteriors a profile which is shaped to complement the profile of a receiver of a standardized head clamp holding device.

* * * * *